(12) United States Patent
Perdue et al.

(10) Patent No.: US 10,835,335 B2
(45) Date of Patent: Nov. 17, 2020

(54) CABLE FAILURE DETECTION

(71) Applicant: Ethicon LLC, Guaynabo, PR (US)

(72) Inventors: David Perdue, Montgomery, OH (US); Jain Hitesh, Maharashtra (IN); Robert Householder, Lebanon, OH (US); Gregory Skinner, West Chester, OH (US); Joshua Dean Young, Loveland, OH (US)

(73) Assignee: Ethicon LLC, Guaynabo, PR (US)

( * ) Notice: Subject to any disclaimer, the term of this patent is extended or adjusted under 35 U.S.C. 154(b) by 233 days.

(21) Appl. No.: 15/918,793

(22) Filed: Mar. 12, 2018

(65) Prior Publication Data

US 2019/0274769 A1  Sep. 12, 2019

(51) Int. Cl.
*A61B 34/00* (2016.01)
*A61B 34/30* (2016.01)
*A61B 17/04* (2006.01)
*A61B 17/072* (2006.01)
*A61B 17/29* (2006.01)
*A61B 90/00* (2016.01)
*A61B 34/20* (2016.01)
*A61B 17/00* (2006.01)

(52) U.S. Cl.
CPC .......... *A61B 34/71* (2016.02); *A61B 17/0469* (2013.01); *A61B 17/07207* (2013.01); *A61B 17/29* (2013.01); *A61B 34/30* (2016.02); *A61B 2017/00017* (2013.01); *A61B 2017/00123* (2013.01); *A61B 2017/00323* (2013.01); *A61B 2017/00398* (2013.01); *A61B 2034/2059* (2016.02); *A61B 2034/302* (2016.02); *A61B 2090/064* (2016.02); *A61B 2090/066* (2016.02); *A61B 2090/0809* (2016.02); *A61B 2560/0276* (2013.01)

(58) Field of Classification Search
CPC ..... A61B 17/29; A61B 34/71; A61B 17/0469; A61B 34/30
See application file for complete search history.

(56) References Cited

U.S. PATENT DOCUMENTS

| | | | | |
|---|---|---|---|---|
| 2002/0087148 A1* | 7/2002 | Brock | ................ | A61B 17/0469 606/1 |
| 2004/0106916 A1* | 6/2004 | Quaid | .................. | G06F 3/0346 606/1 |
| 2005/0075538 A1* | 4/2005 | Banik | ................ | A61B 1/00071 600/141 |
| 2006/0105168 A1* | 5/2006 | Willemsen | ............. | D06M 11/76 428/357 |

(Continued)

*Primary Examiner* — Richard G Louis
(74) *Attorney, Agent, or Firm* — Mintz Levin Cohn Ferris Glovsky and Popeo, P.C.

(57) ABSTRACT

Systems and methods for monitoring one or more cables of surgical tools are provided. The systems generally include a surgical tool with an end effector that has at least one function and a drive system that is operably coupled to the end effector and operably coupled to at least one motor. The drive system has at least one cable, and the drive system is configured to drive the at least one function on the end effector through actuation of the at least one cable. A control system is configured to actuate the at least one motor to drive the drive system and to preemptively detect failure of the at least one cable of the drive system.

15 Claims, 11 Drawing Sheets

(56) References Cited

U.S. PATENT DOCUMENTS

| | | | |
|---|---|---|---|
| 2007/0173788 A1* | 7/2007 | Schena | A61B 34/30 606/1 |
| 2008/0065111 A1* | 3/2008 | Blumenkranz | B25J 15/0009 606/130 |
| 2008/0287963 A1* | 11/2008 | Rogers | A61B 1/00039 606/130 |
| 2011/0089388 A1* | 4/2011 | Kiova | B66D 1/505 254/267 |
| 2011/0144517 A1* | 6/2011 | Cervantes | A61B 5/08 600/538 |
| 2014/0088612 A1* | 3/2014 | Bartol | A61B 5/6852 606/130 |
| 2018/0049819 A1 | 2/2018 | Harris et al. | |
| 2018/0049820 A1 | 2/2018 | Widenhouse et al. | |
| 2018/0064498 A1 | 3/2018 | Kapadia et al. | |

* cited by examiner

CABLE FAILURE DETECTION

FIELD

Devices, methods, and systems for cable failure detection in surgical devices are provided herein, such as through cable breakage detection.

BACKGROUND

More and more surgical procedures are being performed using electrically-powered surgical devices that are either hand-held or that are coupled to a robotic surgical system. Such devices generally include one or more motors for driving various functions on the device, such as shaft rotation, articulation of an end effector, scissor or jaw opening and closing, firing or clips, staples, cutting elements, and/or energy, etc.

Electrically-powered surgical devices, especially robotic devices, are often cable-driven and reusable. The devices are often rated on the number of procedures that they can perform, but it is difficult to determine exactly when a device might fail because devices are used in a variety of procedures and surgeons utilize a variety of preferred techniques during such procedures. Failure of a device is often controlled by failure of one or more cables in the device because many devices use cables to drive functionality in the device. As a device is used over multiple procedures, cables can become frayed or worn, leading to the chance of cable failure. Detecting when this failure is about to occur can allow surgeons to extract and replace the device and avoid potential harm to a patient.

Accordingly, there remains a need for improved devices and methods that allow for detection of failure in a surgical device, such as through cable break detection.

SUMMARY

Devices, methods, and systems for cable failure detection are provided herein.

In one aspect, a robotic surgical system is provided that includes an end effector assembly with a shaft that has an end effector disposed at a proximal end thereof. The end effector has at least one function. A drive system is operably coupled to the end effector assembly and is also operably coupled to at least one motor, and the drive system has at least one cable. The drive system is configured to drive the at least one function on the end effector through actuation of the at least one cable. A control system is configured to actuate the at least one motor to drive the drive system and thereby control actuation of the at least one function of the end effector. The control system is also configured to preemptively detect potential imminent failure of the at least one cable of the drive system.

The system can vary in numerous ways. For example, the end effector assembly can include a torque sensor operably coupled with the at least one motor. The control system can also be configured to record force applied to the cable by the motor and calculate a derivative of force applied to the cable. In another example, the control system can be configured to alert a user if the derivative of force applied to the cable exceeds a predetermined threshold value. The threshold value can be determined by recording a running average of the derivative of force. In another embodiment, the end effector assembly can include a rotary encoder. The control system can be configured to record a position of the cable, calculate a derivative of position of the cable, and alert a user if the derivative of position exceeds a threshold value. In another example, the at least one cable can include a sacrificial filament therein, and the sacrificial filament can be configured to fail at a lower force relative to remaining filaments in the at least one cable.

In another aspect, a surgical tool is provided that has a housing and an end effector assembly with a shaft that has an end effector disposed at a proximal end thereof. The end effector has at least one function, and the end effector assembly is operationally engageable with the housing. A drive system is operably coupled to the end effector assembly and is also operably coupled to at least one motor. The drive system has at least one cable, and the system is configured to drive the at least one function on the end effector through actuation of the at least one cable. A control system is disposed in the housing and is in communication with the motor and one or more sensors in the surgical tool. The control system is configured to actuate the at least one motor to drive the drive system, and it is configured to monitor a status of the at least one cable based on data from the sensors.

The tool can have a variety of embodiments. For example, the surgical tool can have a first, normal mode of operation and a second, alert mode of operation, and the control system can be configured to transition the surgical tool from the first mode to the second mode upon detecting an imminent failure of the at least one cable when monitoring the status of the cable based on the data from the sensors. In another example, the sensors can include at least one of a torque sensor and a rotary encoder. The control system can be configured to record at least one of a force on or a position of the cable, calculate a derivative value of the recorded value, and alert a user if the derivative value exceeds a predetermined threshold value. In one embodiment, the predetermined threshold value can be a multiple of a running average of the derivative value. In another embodiment, the at least one cable can include a sacrificial filament therein, and the sacrificial filament can be configured to fail at a lower force relative to remaining filaments in the at least one cable. In still another example, the end effector can include one of a stapler, a cutter, a grasper, or a suturing head. The at least one function of the end effector can be articulation of the end effector.

In another aspect, a method is provided that includes operating a surgical tool under normal operating conditions, during which a control system of the surgical tool monitors an integrity indicator of one or more cables therein and alerts a user of an imminent cable failure of the one or more cables. The method also includes removing the surgical tool upon being alerted by the control system of an imminent cable failure of the one or more cables.

The method can have numerous variations. For instance, the control system can monitor at least one of torque and rotation of one or more motors in the surgical tool using one or more sensors. The control system can also calculate derivatives of at least one of force and position of the one or more cables based on values from the torque and rotation of the one or more motors, and the control system can detect when a current value of one or both of the derivatives of force and position exceeds a threshold value. When the control system detects potential for an imminent cable failure of the one or more cables, the surgical tool can enter a safe mode of operation.

BRIEF DESCRIPTION OF DRAWINGS

This invention will be more fully understood from the following detailed description taken in conjunction with the accompanying drawings, in which.

DETAILED DESCRIPTION

Figure 1:
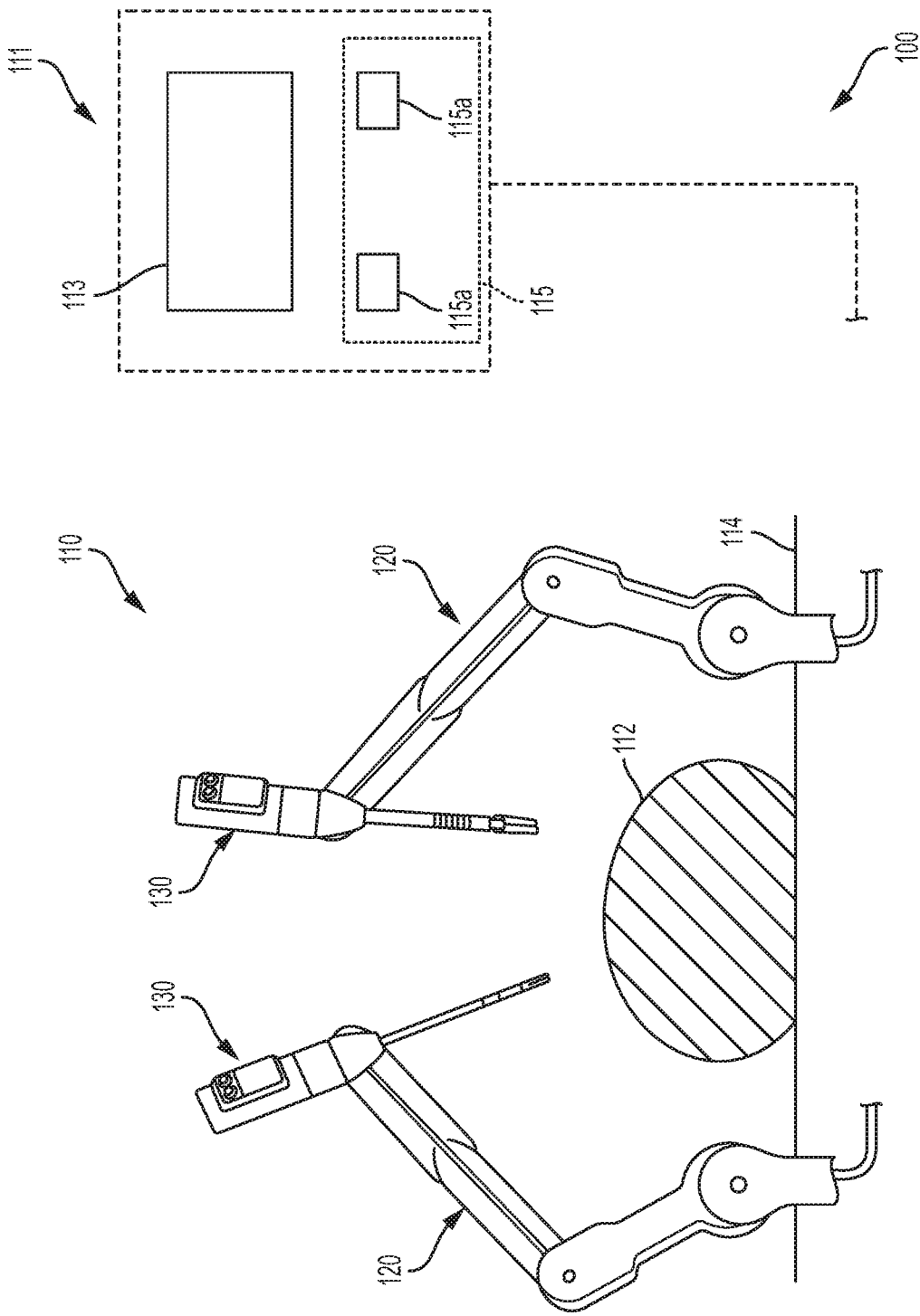
FIG. 1 is a perspective view of an embodiment of a surgical robotic system.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

A variety of surgical procedures use one or more electronic surgical devices that are actuated by a series of motors, gears, and cables. This is particularly true in robotic and/or minimally-invasive surgeries when an end effector, such as a stapler, cutter, grasper, suturing head, etc., is positioned at a distal-most end of a surgical device within a patient while motors used to actuate the end effector are positioned proximally away from the end effector and outside of the patient. In such cases, a user actuates one or more motors through a variety of actuation means to cause various functions to occur at the remotely-placed end effector, and the user relies on motors to actuate gears and cables within the device to translate that actuation motion to the end effector. Many electronic surgical devices are reusable, however, and the cables translating motion and functionality throughout the device can wear out over the lifetime of the device. Most electronic surgical devices are rated on the number of uses for this reason. As the device is used, it is more likely that one or more cables within the device will fail. Cables are typically made of a plurality of filaments or strands that are woven together, and repeated use of the surgical devices can cause the filaments to fray and eventually break. Once a single filaments breaks, load on the remaining filaments in a cable rapidly increases, which causes additional filaments to break and quickly results in a catastrophic failure in which the entire cable breaks and the device is no longer operable. In such situations, a patient may be harmed or a procedure may have to be aborted if a device fails while the end effector is actively carrying out a function within the patient.

Accordingly, devices, systems, and methods for detecting an impending cable failure or breakage are provided herein. The systems and methods can be used in connection with various end effectors involved in robotic surgery or non-invasive surgery, for example a linear stapler, a circular stapler, a cutting member, a sealing member, a grasping member, a suturing member, etc. In an exemplary embodiment, a robotic surgical system can include an end effector assembly with a shaft that has an end effector disposed at a proximal end thereof. The end effector can have at least one function, for example stapling tissue, cutting tissue, sealing tissue through application of electrical energy, suturing tissue through application of at least one suture, grasping tissue, rotating or articulating the end effector, etc. A drive system can be operably coupled to the end effector assembly and operably coupled to at least one motor. The drive system can have one or more cables engaged thereto and one or more gears engaged thereto so that the drive system can be configured to drive the at least one function (e.g., articulation of the end effector) on the end effector through actuation of the cable(s) and/or gear(s). A control system can be configured to actuate the at least one motor to drive the drive system and thereby control movement of the end effector and/or actuation of the at least one function of the end effector. The control system can be configured to detect an imminent failure of at least one cable of the drive system, as discussed in more detail below. Because the system can detect an imminent failure of a cable that is responsible for driving one or more functions in the end effector, a user can respond appropriately to the imminent failure, for example by disabling the device, placing the device in some form of a safety mode, extracting the device from a patient and replacing the device, etc. The control system can thus be configured to monitor the health and/or one or more integrity indicators of one or more cables.

Additional details regarding the operation and design of common end effectors, such as surgical staplers, are disclosed in U.S. Pat. Nos. 8,469,252, 8,602,286 and 9,713,468, each of which is incorporated herein by reference in its entirety.

Robotic Surgical System

The systems, devices, and methods disclosed herein can be implemented using a robotic surgical system. A person skilled in the art will also appreciate that all electronic communication in the system can be wired, all electronic communication in the system can be wireless, or some portions of the system can be in wired communication and other portions of the system can be in wireless communication.

FIG. 1 is a perspective view of one embodiment of a surgical robotic system 100 that includes a patient-side portion 110 that is positioned adjacent to a patient 112, and a user-side portion 111 that is located a distance from the patient, either in the same room and/or in a remote location. The patient-side portion 110 generally includes one or more robotic arms 120 and one or more tool assemblies 130 that are configured to releasably couple to the robotic arm 120. The user-side portion 111 generally includes a vision system 113 for viewing the patient 112 and/or surgical site, and a control system 115 with inputs 115a for controlling the movement of the robotic arms 120 and each tool assembly 130 during a surgical procedure.

The control system 115 can have a variety of configurations and it can be located adjacent to the patient, e.g., in the operating room, remote from the patient, e.g., in a separate control room, or it can be distributed at two or more locations. For example, a dedicated system control console can be located in the operating room, and a separate console can be located in a remote location. The control system 115 can include components that enable a user to view a surgical site of a patient 112 being operated on by the patient-side portion 110 and/or to control one or more parts of the patient-side portion 110 (e.g., to perform a surgical procedure at the surgical site of the patient 112). In some embodiments, the control system 115 can also include one or more manually-operated input devices, such as a joystick, exo-skeletal glove, a powered and gravity-compensated manipulator, or the like. These input devices can control teleoperated motors which, in turn, control the movement of the surgical system, including the robotic arms 120 and tool assemblies 130.

The patient-side portion can also have a variety of configurations. As depicted in FIG. 1, the patient-side portion 110 couples to an operating table 114. However, in some embodiments, the patient-side portion 110 can be mounted to a wall, to the ceiling, to the floor, or to other operating room equipment. Further, while the patient-side portion 110 is shown as including two robotic arms 120, more or fewer robotic arms may be included, and a variety of different robotic arms can be included, as discussed in detail below. Furthermore, the patient-side portion 110 can include separate robotic arms 120 mounted in various positions, such as relative to the surgical table 114 (as shown in FIG. 1). Alternatively, the patient-side portion 110 can include a single assembly that includes one or more robotic arms 120 extending therefrom.

Figure 2:
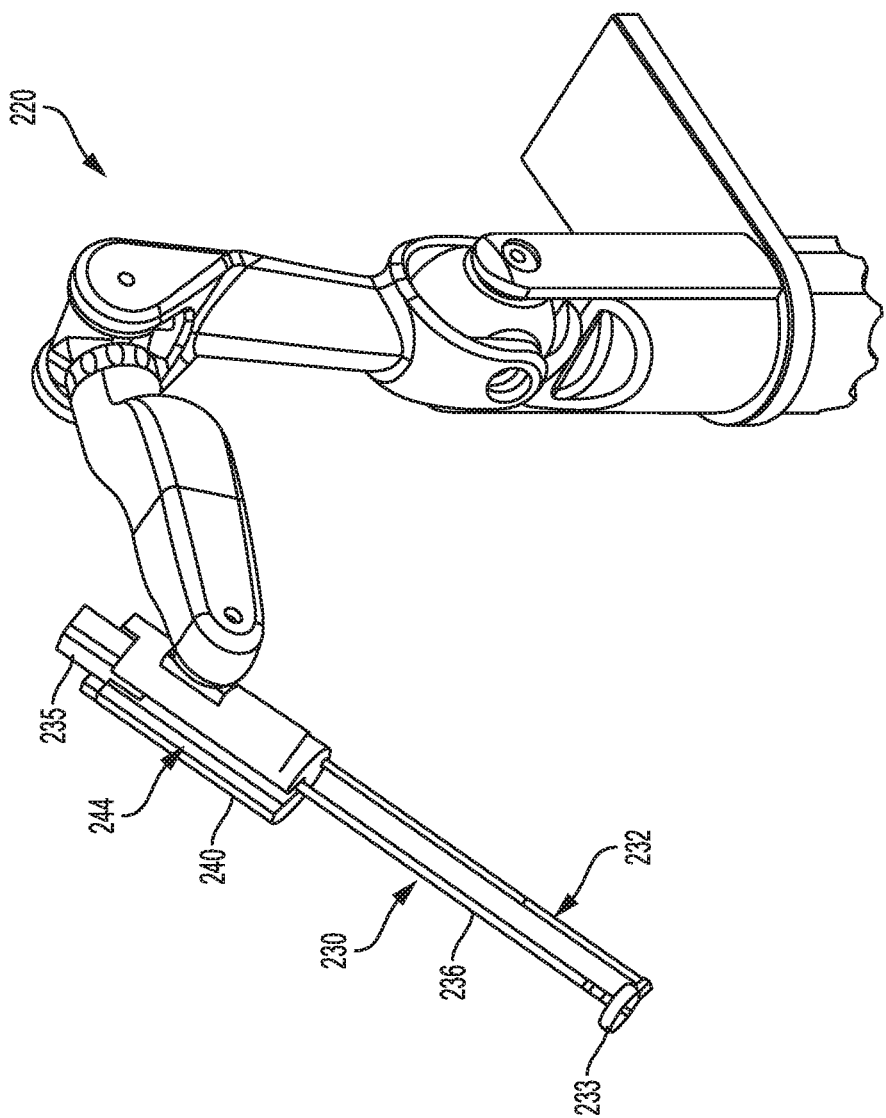
FIG. 2 illustrates an embodiment of the robotic arm of FIG. 1 having an embodiment of a tool assembly releasably coupled to the robotic arm.

FIG. 2 illustrates an embodiment of a robotic arm 220 and a tool assembly 230 releasably coupled to the robotic arm 220, both of which can be incorporated into a surgical robotic system such as the surgical robotic system 100 along with or in replacement of the robotic arms 120 and tool assemblies 130. The robotic arm 220 support and move the associated tool assembly 230 along one or more mechanical degrees of freedom (e.g., all six Cartesian degrees of freedom, five or fewer Cartesian degrees of freedom, etc.).

The robotic arm 220 includes a tool driver 240 at a distal end of the robotic arm 220, which can assist with controlling features associated with the tool assembly 230. The robotic arm 220 also includes a movable tool guide 232 that can retract and extend relative to the driver 240. A shaft of the tool assembly 230 extends parallel to a threaded shaft of the movable tool guide 232 and can extend through a distal end feature 233 (e.g., a ring) of the movable tool guide 230 and into a patient.

In order to provide a sterile operation area while using the surgical system, a barrier (not shown) can be placed between the actuating portion of the surgical system (e.g., the robotic arm 220) and the surgical instruments (e.g., the tool assembly 230) in the sterile surgical field. A sterile component, such as an instrument sterile adapter (ISA), can also be placed at the connecting interface between the tool assembly 230 and the robotic arm 220. The placement of an ISA between the tool assembly 230 and the robotic arm 220 can ensure a sterile coupling point for the tool assembly 230 and the robotic arm 220. This permits removal of tool assemblies 230 from the robotic arm 220 to exchange with other tool assemblies 230 during the course of a surgery without compromising the sterile surgical field.

Figure 3:
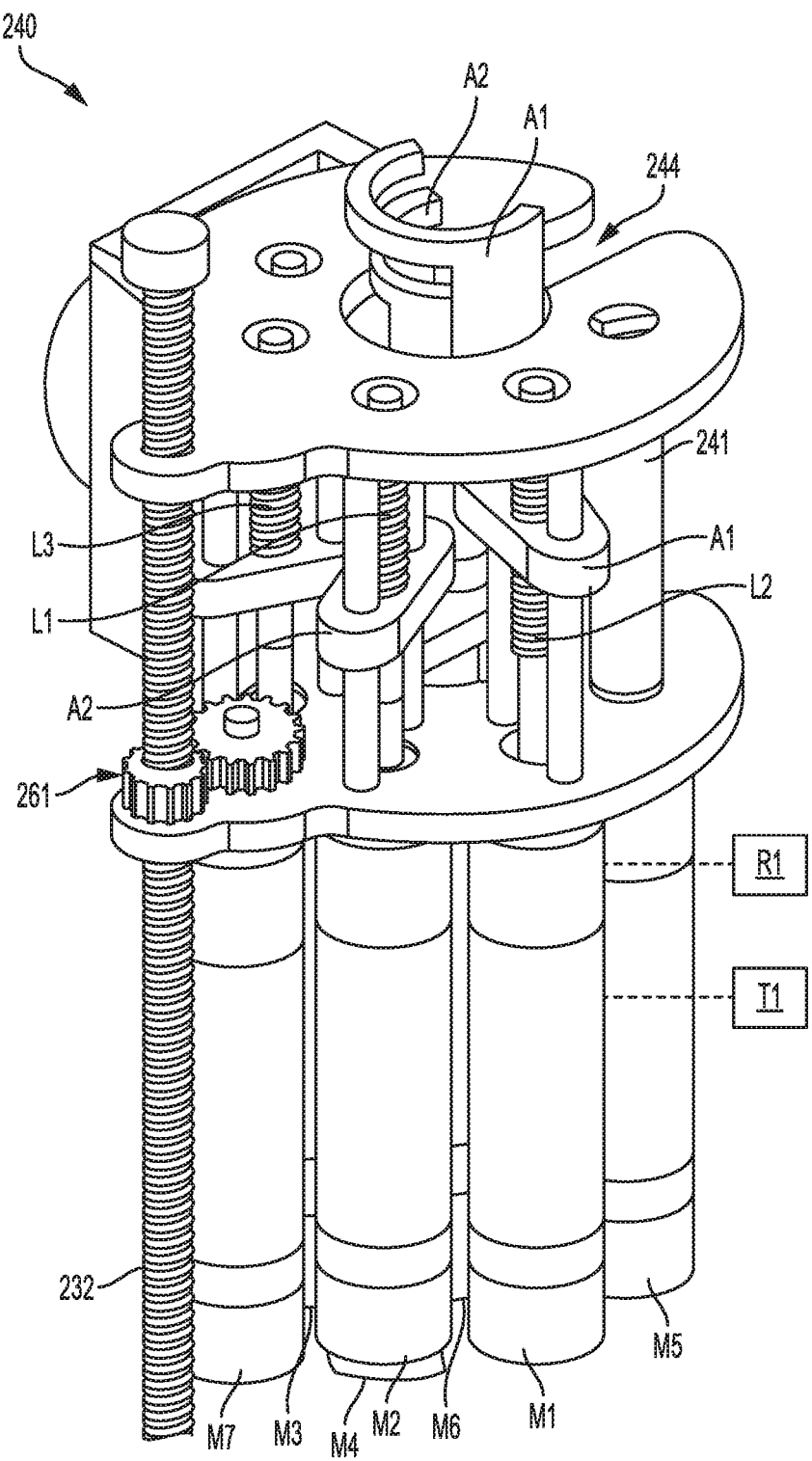
FIG. 3 illustrates an embodiment of a tool driver engageable with the tool assembly of FIG. 2.

FIG. 3 illustrates the tool driver 240 in more detail. As shown, the tool driver 240 includes one or more motors, e.g., seven motors M1-M7 are shown, that control a variety of movements and actions associated with the tool assembly 230, as will be described in greater detail below. The driver 240 also includes one or more lead screws (e.g., three lead screws L1, L2, and L3 are shown) that can be individually rotated by a motor and, as a result of the rotation of the lead screw, cause linear and/or rotational movement of at least one actuator (e.g., see, for example, actuators A1 and A2 shown in FIG. 3). Movement of each actuator controls the movement of driving members (e.g., gears, cables) located in the tool assembly 230 for controlling one or more actions and movements that can be performed by the tooling assembly 230, such as for assisting with performing a surgical operation. The actuators extend from an end of the driver 240 for coupling to the driving members of the tool assembly 230 mounted on the tool driver 240. The tool assembly 230 is loaded from a top side of the driver 240 with the shaft of the tool assembly 230 being positioned in a shaft-receiving channel 244 formed along the side of the driver 240. The shaft-receiving channel 244 allows the shaft, which extends along a central axis of the tool assembly 230, to extend along a central axis of the driver 240 when the tool assembly 230 is coupled to the driver 240. In other embodiments, the shaft can extend through on opening in the tool driver 240, or the two components can mate in various other configurations.

Figure 4:
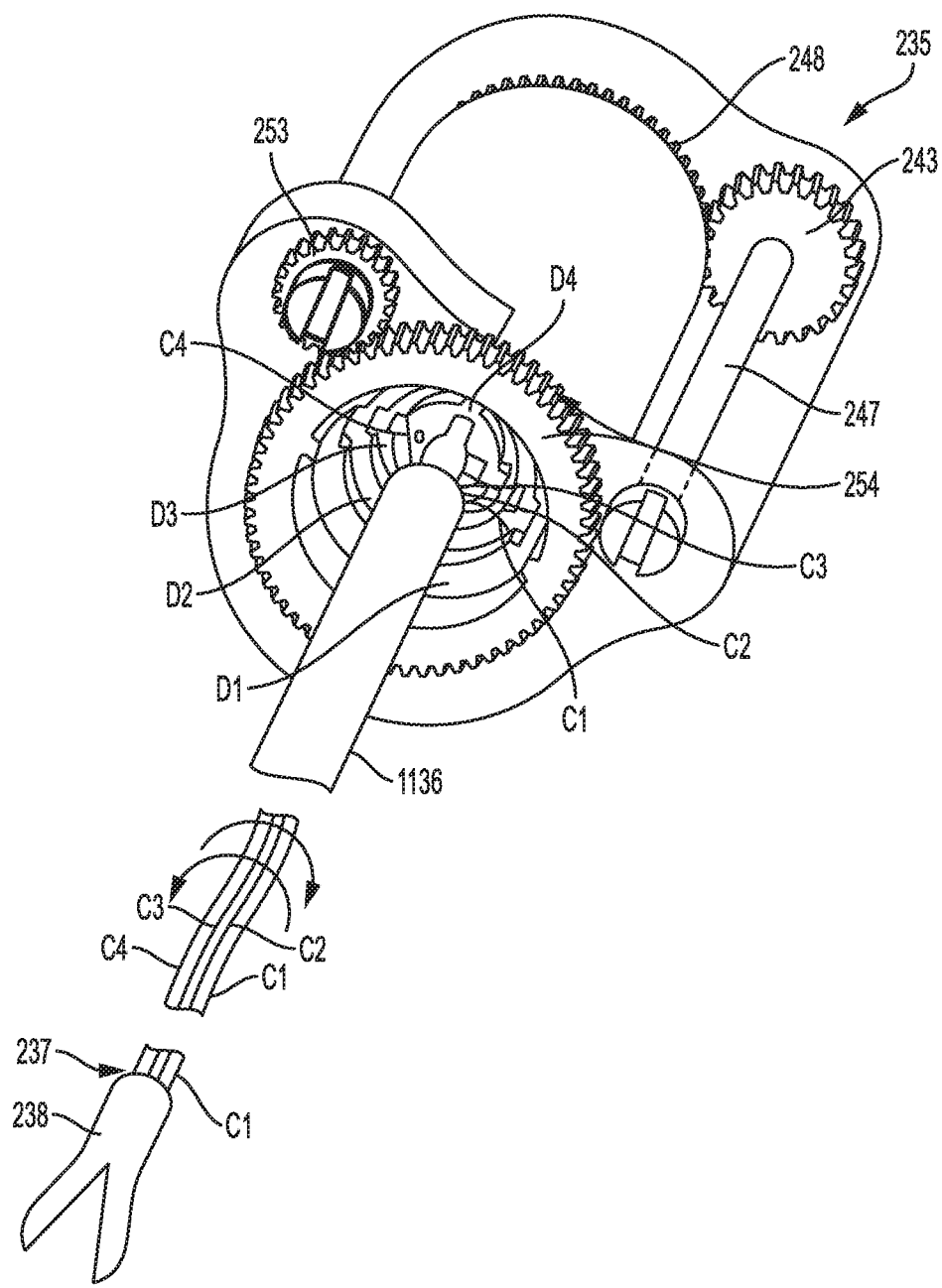
FIG. 4 illustrates a portion of a puck actuation assembly contained within the tool assembly of FIG. 2.

As shown in FIGS. 2 and 4, the tool assembly 230 includes a puck or housing 235 coupled to a proximal end of a shaft 236 and an end effector 238 coupled to a distal end of the shaft 236. The housing 235 includes coupling features that assist with releasably coupling the puck 235 to the tool driver 240 of the robotic arm 220. The housing 235 includes driving members (e.g., gears, cables, and/or drivers) that can be directly or indirectly actuated by the one or more motors M1-M7, as will be described in greater detail below. The driving members in the housing 235 control the operation of various features associated with the end effector 238 (e.g., clamping, firing, rotation, articulation, etc.), as well as control the movement of the shaft 236 (e.g., rotation and/or articulation of the shaft).

The shaft 236 can be releasably coupled to the housing 235 such that the shaft 236 can be interchangeable with other shafts. This can allow a single housing 235 to be adaptable to various shafts 236 having different end effectors 238. The shaft 236 also includes actuators and connectors that extend along the shaft and assist with controlling the actuation and/or movement of the end effector 238 and/or shaft 236. The shaft 236 includes one or more joints or wrists 237 that allow a part of the shaft 236 or the end effector 238 to rotate and/or articulate relative to the longitudinal axis of the shaft 236. This can allow for fine movements and various angulation of the end effector 238 relative to the longitudinal axis of the shaft 236. The end effector 238 can include any of a variety of surgical tools, such as a stapler, a clip applier, forceps, a needle driver, a cautery device, a cutting tool, a pair of jaws, an imaging device (e.g., an endoscope or ultrasound probe), or a combined device that includes a combination of two or more various tools.

FIG. 4 illustrates a part of a housing actuation assembly contained within the housing 235. As shown in FIG. 4, the housing 235 includes at least one drive system or driving member (e.g., four driving members D1, D2, D3, and D4 are shown) that can each become engaged with an actuator of the driver 240 such that actuation of an actuator causes actuation of a driving member thereby controlling the operation of various features associated with the shaft 236 and/or end effector 238. Each driving member D1-D4 is coupled to a proximal end of a shaft or cable (e.g., four cables C1, C2, C3, and C4 are shown). Each cable can extend from a driving member and couple to a feature associated with either the shaft 236 or the end effector 238 thereby controlling a function of such feature.

Figure 5:
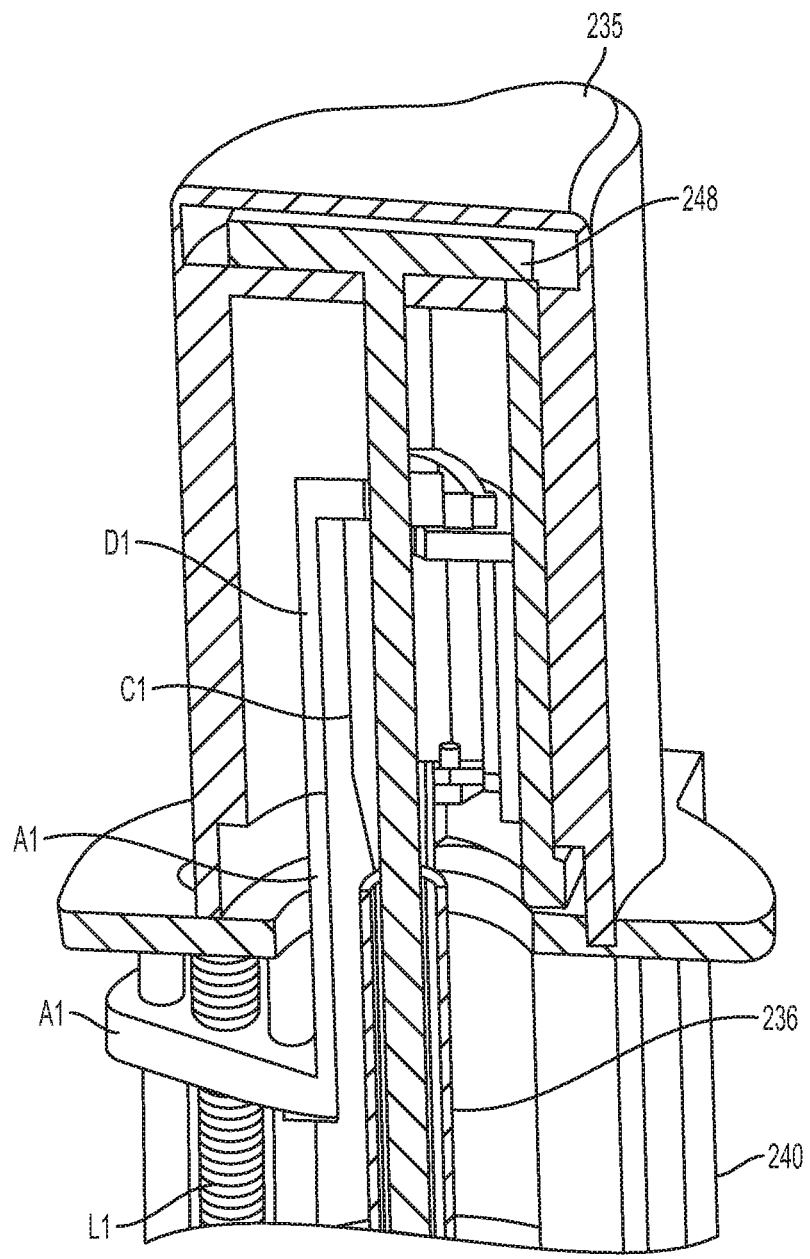
FIG. 5 illustrates the tool assembly of FIG. 2 coupled to the driver of FIG. 3 with actuators extending from the driver into the puck and engaging a driving member.

FIG. 5 illustrates the housing 235 coupled to the driver 240 with the actuators extending from the driver 240 into the puck 235 and engaging the driving members. Motor M1 causes lead screw L1 to rotate thereby causing actuator A1, which is threadably coupled to lead screw L1, to linearly advance in the proximal direction (towards and into the puck 235). Actuator A1 includes an extension threadably coupled to the lead screw L1. The extension can be coupled to or integrated with a partial cylindrical shaft that extends along the longitudinal axis of the housing 235 and the driver 240. The partial cylindrical shaft of the actuator A1 engages with driving member D1 such that when the actuator A1 is linearly advanced, the driving member D1 is caused to linearly advance in the same direction. Driving member D1 is coupled to cable C1 such that when driving member D1 is advanced in the proximal direction, cable C1 is pulled in the proximal direction. Cable C1 extends along the shaft of the tool assembly 230 and is operatively coupled to a part of the end effector 238 thereby controlling a function of the end effector 238 (e.g., opening and closing of jaws, deployment of a staple, etc.) when the cable is C1 translated in either the proximal or distal direction.

Thus, four motors (e.g., M1-M4) each individually control movement of a respective lead screw (e.g., L1-L4) thereby individually linearly translating a respective actuator (e.g., A1-A4) coupled thereto. Although the actuators are described as being linearly translated, the actuators can be linearly translated and/or rotationally moved as a result of actuation of a respective motor. Additional motors (e.g., motors M5 and M6) are included in the driver 240 for actuating various other aspects of the tool assembly 230. For example, motor M5 causes a first driver shaft 241 to rotate, which is operatively coupled to a first housing shaft 247 having a first housing gear 243 coupled to a distal end of the first puck shaft 247. Rotation of the first driver shaft 241 thereby causes the first housing shaft 247 and first housing gear 243 to rotate. The first housing gear 243 is engaged with a first shaft rotation gear 248 that is caused to rotate as a result of the first housing gear 243 rotating. The first shaft rotation gear 248 is operatively coupled to the shaft 236 of the tool assembly 230 and can thereby cause rotation of the shaft 236 and/or end effector 238. Motor M6 causes a second driver shaft to rotate, which is operatively coupled to a second puck gear 253. The second housing gear 253 is engaged with a second shaft rotation gear 254 that is caused to rotate as a result of the second puck gear 253 rotating. The second shaft rotation gear 254 is also operatively coupled to the shaft 236 and, upon rotation, provides additional torque through the shaft 236 and for various features associated with the end effector 238. Actuation of motor M7 causes shaft gears 261 to rotate, thereby causing the threaded shaft of the movable tool guide 232 to linearly translate. Additional details on robotic systems can be found in U.S. patent application Ser. No. 15/237,712 and U.S. patent application Ser. No. 15/237,740, both of which were filed on Aug. 16, 2016 and are incorporated herein in their entirety. This continued actuation and use of the various internal components of the tool assembly 230 leads to wear and tear of the components themselves and eventual deterioration of the overall tool assembly 230.

Imminent Failure Detection

As the robotic system 100 is used, components in the tool assembly 230 will deteriorate, and the cables in particular will experience wear and possible failure, as discussed above. Cables used to control actuation of an end effector are particularly susceptible to wear and failure. Thus, the control system 115 is configured to detect an imminent failure of at least one cable, such as the cables C1-C4, through collecting and monitoring data about the system 100 and the various surgical tools used therein, such as the tool assembly 230. The control system 115 is thus configured to monitor the health and/or one or more integrity indicators of one or more cables of the cables C1-C4.

As the motors M1-M7 operate, a variety of data about one or more of the motors M1-M7 can be monitored, recorded, analyzed, and transmitted to the control system 115. This data can include force, torque, position, applied voltage, applied current, etc. As illustrated in FIG. 3, one or more rotary encoders, such as rotary encoder R1, and one or more torque sensors, such as torque sensor T1, are operatively coupled to one or more motors, such as the motor M1, and communicate data to the control system 115. The rotary encoder R1 and the torque sensor T1 allow the system 100 to directly monitor rotation of and force applied by the motor M1. However, through data of the rotary encoder R1 and the torque sensor T1 about the motor M1, the system 100 is configured to indirectly monitor applied force and position of the cable C1 because the motor M1 provides force and movement to the cable C1 through the driving member D1.

Figure 6:
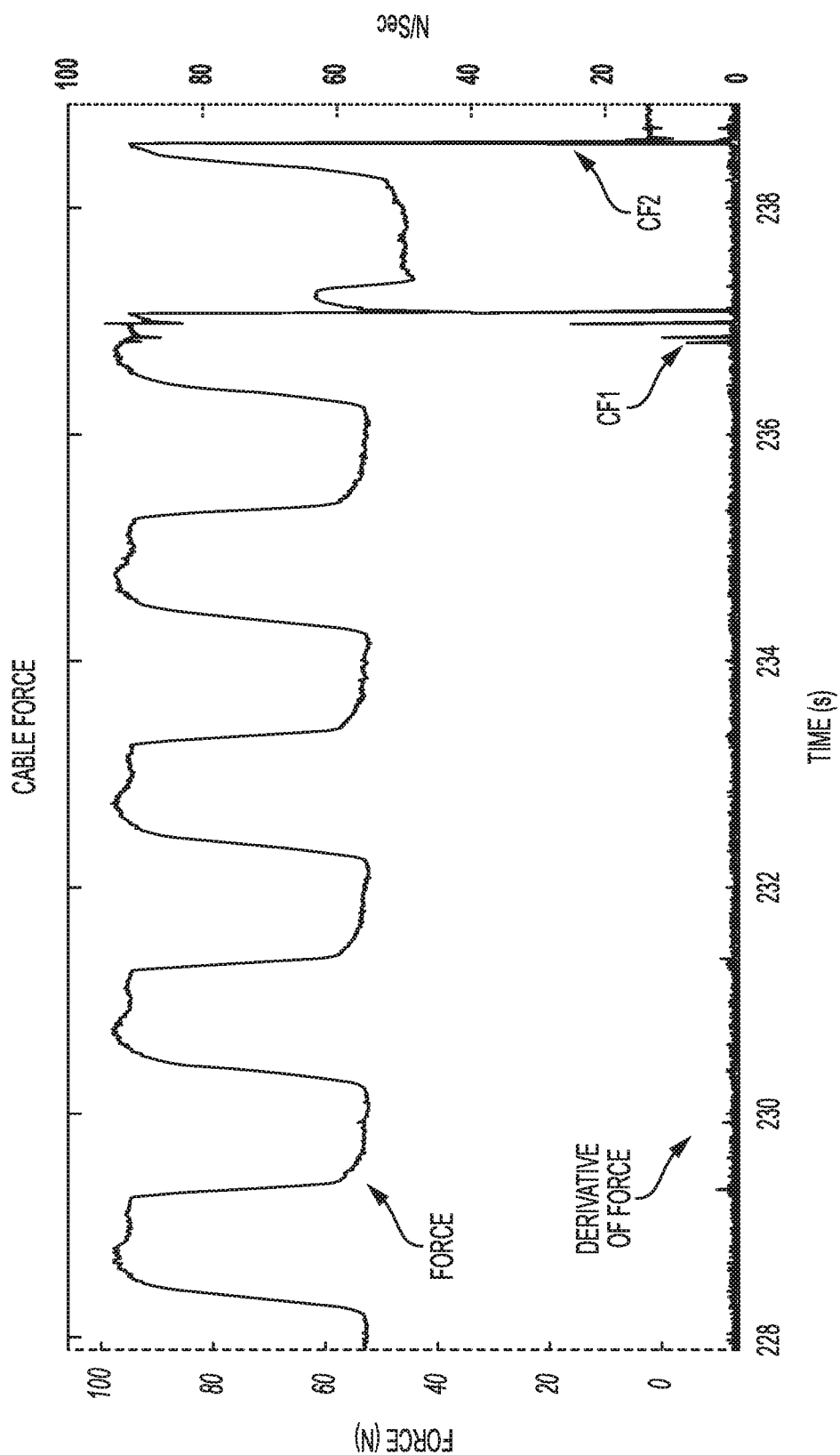
FIG. 6 is a graph illustrating force and a derivative of force over time applied to a cable in the tool assembly of FIG. 2.

As the system 100 monitors the force and position of the cable C1, the system 100 is configured to monitor the potential for an imminent break in a (e.g., cable C1) by analyzing at least one of two pieces of information: the derivative of the force applied to the cable C1 and the derivative of the position of the cable C1. As illustrated in FIG. 6, force applied to the cable C1 is monitored over time, and the value of applied force is expected to transition smoothly from one moment to the next under normal conditions. However, at a first point of imminent cable failure CF1 when a single filament or a small bundle of filaments fail but the cable C1 is otherwise operable and the tool assembly 230 is still able to operate normally, a small change in the applied force can be detected. However, the derivative of the force on the cable C1 is also calculated and monitored by the system 100, and when the derivative of the applied force is taken, a very noticeable spike is present at the first imminent cable failure point CF1, as illustrated in FIG. 6. The magnitude of this signal can be significantly greater than the preceding derivative values. As illustrated in FIG. 6, the value is greater than 10 times the normal profile of the preceding derivative values. If the tool assembly 230 continues to be operated under normal conditions, a catastrophic failure point CF2 will be reached by the cable C1, in which the entire cable C1 fails, and this failure point can be detected by the system 100. However, catastrophic failure point CF2 represents a complete break of cable C1, and the tool assembly 230 may be partially or entirely inoperable at this point should this point be reached. User may have to halt the surgery and extract the assembly 230 or take other drastic measures to remove and replace the assembly 230, potentially harming the patient and further damaging equipment. The system 100 is thus configured to monitor for a significant change in the calculated derivative of force on the cable C1, and when such a change is detected, to alert the user of the potential for cable failure. A significant change in the derivative of force can be any noticeable difference in the calculated derivative of force, for example at least a 5-fold change or a 10-fold change or more.

Figure 7:
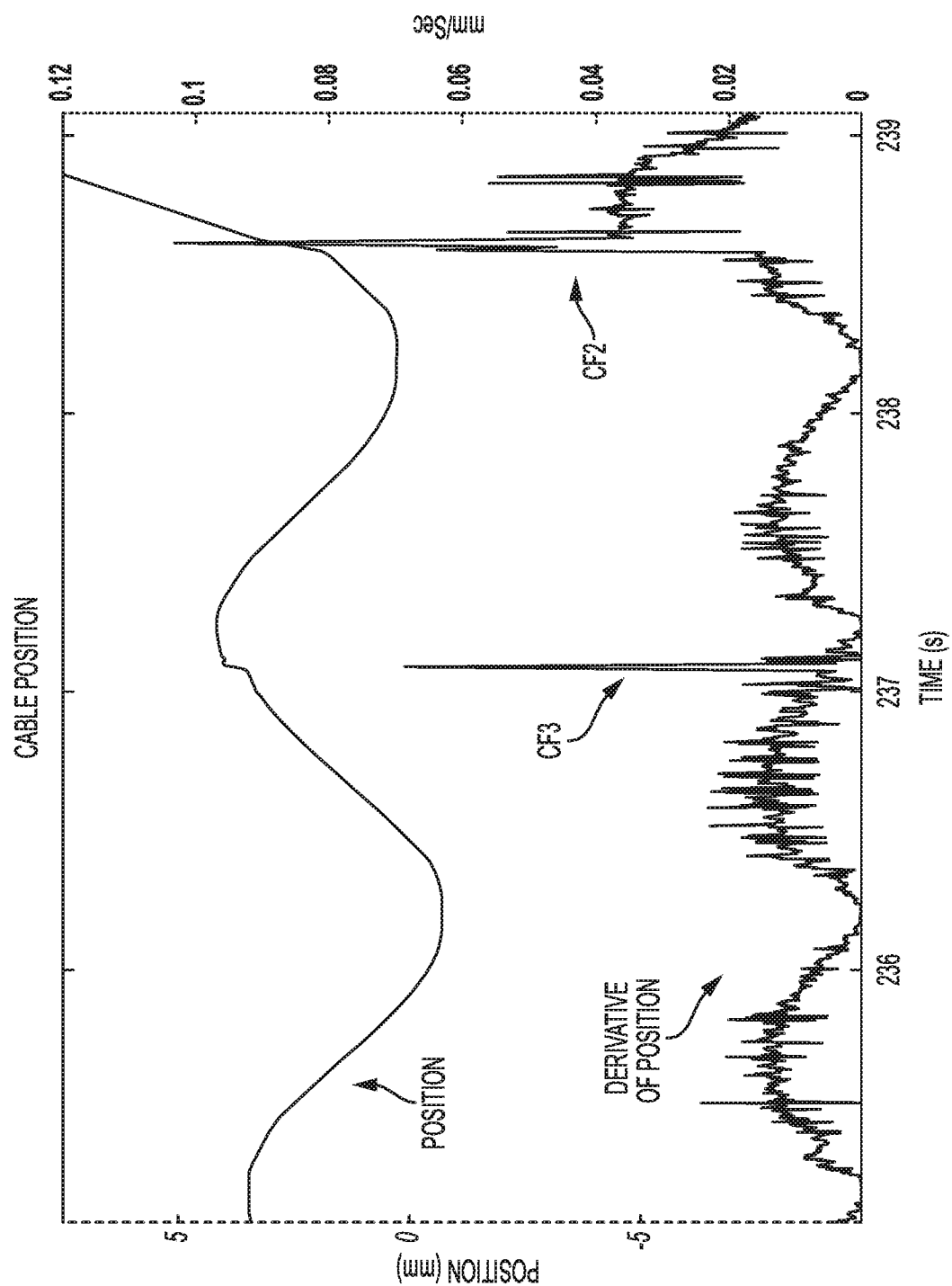
FIG. 7 is a graph illustrating position and a derivative of position over time applied to the cable in the tool assembly of FIG. 2.

As illustrated in FIG. 7, the system 100 is also configured to monitor a position of the cable C1 over time, and the value of the measured position is expected to transition smoothly from one moment to the next. However, around a point of imminent cable failure when a single filament or a small bundle of filaments fail, a small change in the measured position can be detected. Obtaining the derivative of the measured cable position provides the cable velocity. FIG. 7 illustrates a very noticeable spike in this measurement at the second imminent cable failure point CF3. The magnitude of this signal can be significantly greater than the preceding derivative values, for example at least a 5-fold change or a 10-fold change or more. As discussed above, if the tool assembly 230 continues to be operated under normal conditions, the catastrophic failure point CF2 will be reached and detected by the system 100. The system 100 is thus configured to monitor for a significant change in the calculated derivative of position of the cable C1. As can be seen when comparing FIGS. 6 and 7, however, the system 100 detects the first imminent cable failure point CF1 significantly earlier than (e.g., about 1.9 seconds earlier) the catastrophic failure point CF2, while the system 100 detects the second imminent cable failure point CF3 shortly after (e.g., about 200 ms later) the first imminent cable failure point CF1. The catastrophic failure point CF2 is the same failure in both FIGS. 6 and 7; the system 100 is simply able to detect the change in the derivate of force at an earlier point than the change in the derivative of position. Thus, monitoring the derivative of force potentially provides an earlier warning signal than does monitoring of the derivative of position. The system 100 can be configured to preferentially monitor for a significant change in the calculated derivative of force on the cable C1, and to secondarily monitor for a significant change in the calculated derivative of position of the cable C1. However, in other embodiments, the system can monitor only one of the calculated derivative of position and the derivative of force.

While cable C1 is discussed herein, the system 100 can be configured to monitor any of cables C2-C4 in the same way. There can also be a variety of different sensors engaged with the system instead of or in addition to the rotary encoder R1 and/or the torque sensor T1 on the motor M1. For example, additional rotary encoders can be coupled to one or more of the motors M1-M7 to monitor the rotational position of the motor(s) M1-M7, thereby monitoring a rotational or linear movement of a respective drive system and cable(s) coupled to the motor. Alternatively or in addition, a torque sensor can be coupled to one or more of the motors M1-M7 to determine or monitor an amount of force being applied to the motor during device operation. It is also contemplated that other ways to determine or monitor force on the motor(s) can be included, such as measuring current though the motor(s) by using a sensor or a meter device.

When the system 100 is monitoring the derivative of force and/or the derivative of position, a variety of threshold values can be set for each derivative value at which point the system 100 is configured to alert the user of an imminent cable break and/or take some predetermined action. For example, a multiple can be used, in which the system 100 is configured to alert a user if the derivative value exceeds a running average of the previous derivative values by a set multiple, such as by about 5 to 10 times or more. The system 100 can also record an initial running average of the derivative values as a noise level, and it can be configured to filter out the noise and alert a user if the derivative value is more than a set multiple, such as 2 times, higher than the recorded derivate values once the noise has been removed. By taking more immediate readings and by filtering out noise, the system 100 is able to reduce the required threshold multiple to positively identify an impending break. Thus, the threshold can be measured and altered in real time based on feedback from the system 100 and/or preferences of the user, or the threshold can be a fixed value that is set beforehand by a user or manufacturer.

Figure 8:
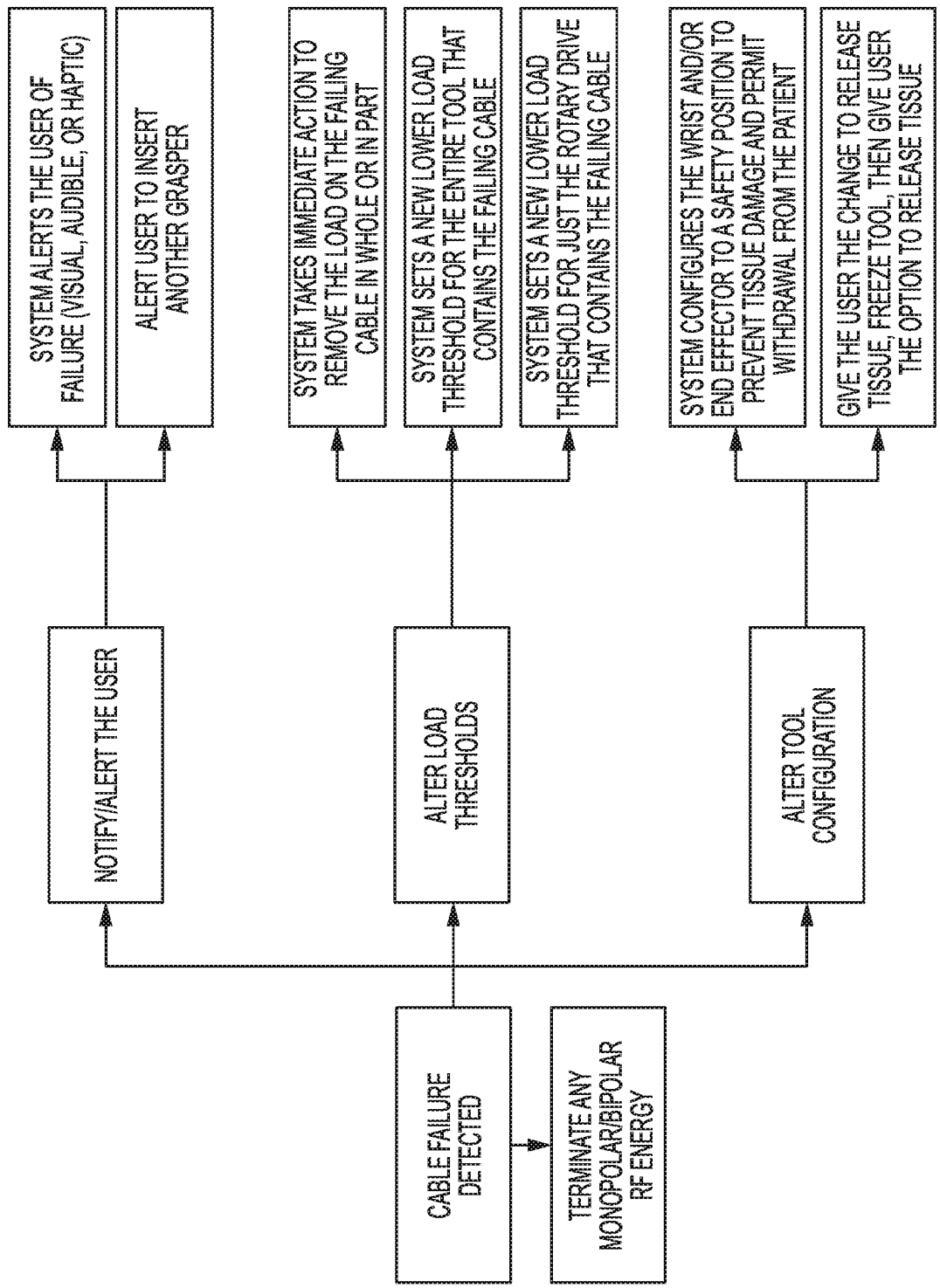
FIG. 8 is a flow chart showing behavior of the robotic system of FIG. 1 in response to failure of a cable filament.

When the system 100 detects an imminent cable failure, the system 100 is configured to take a variety of actions in response, either alone or in conjunction with each other as illustrated in FIG. 8. For example, the system 100 can enter a safe mode of operation that includes performing one or more different actions to assist the user in managing the imminent cable failure. For example, the system 100 can terminate any energy, for example any monopolar/bipolar RF energy being administered to tissue. The system 100 can generate a user alert taking one or more different forms, including but not limited to one or more audible signals, one or more visual signals (e.g., a light, a flashing light, or a textual message), and tactile/haptic signals. The alert can also instruct the user to insert another tool assembly. The system 100 can alter various load thresholds in the tool assembly 230. For example, the system 100 can take immediate action to remove the load being applied on the failing cable in whole or in part. The system 100 can set a new, lower load threshold for the entire tool assembly 230 that contains the failing cable. The system 100 can also set a new, lower load threshold for just an individual rotary drive that contains the failing cable. The system can alter a configuration of one or more tool assemblies being used. For example, the system 100 can configure a wrist and/or an end effector of the tool assembly 230 to enter a safety position to prevent tissue damage and/or to permit withdrawal from the patient (as an example, the system 100 can ensure that jaws on the end effector are closed and any wrist or joints are straight). The system 100 can also reconfigure the tool assembly 230 to allow tissue to be released, at which point the tool assembly 230 can freeze and the user can have the option of releasing tissue. Thus generally, the system 100 can enter a safe mode in which one or more actions can be taken to assist the user in managing the impending cable failure. Alternatively, the system 100 can continue to operate as normal and allow the user to take appropriate action. While a robotic system 100 has been discussed above, the same control system can be incorporated into a handheld surgical device. The device merely requires one or more sensors, as discussed above, and a control system that can monitor derivative values from the sensors and alert a user of an imminent cable failure.

Figure 9:
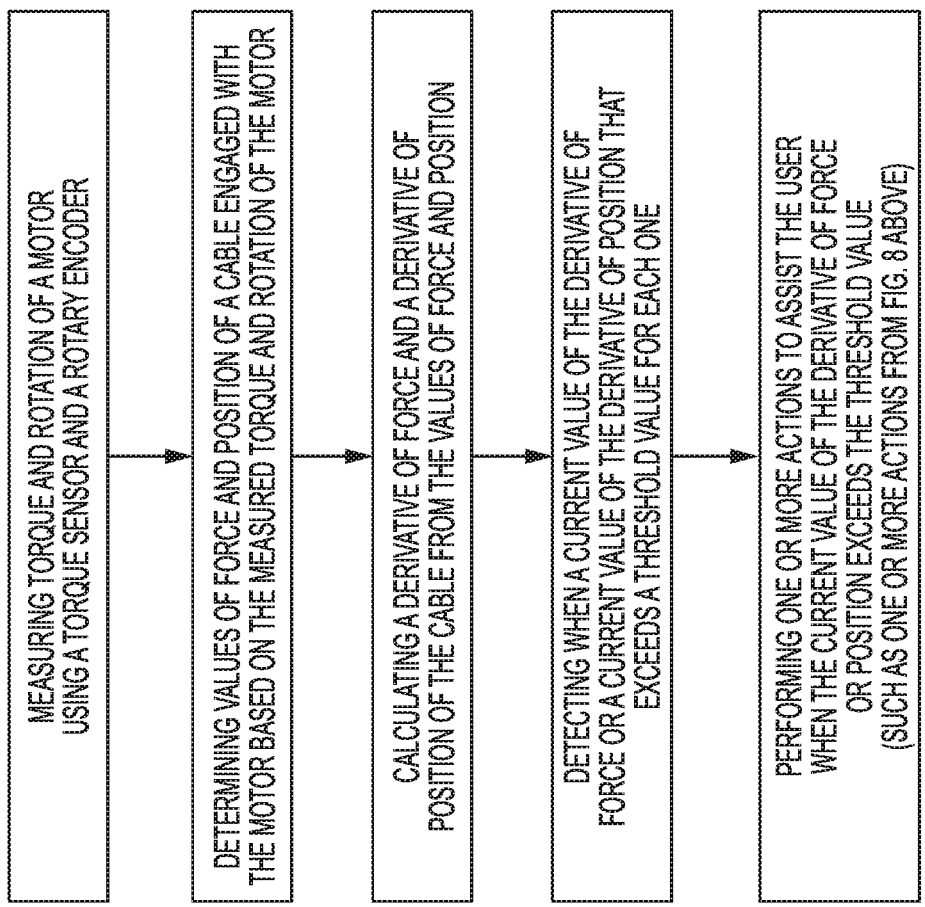
FIG. 9 is a flow chart showing behavior of the robotic system of FIG. 1 during use and imminent failure of a cable filament.

In use as illustrated in FIG. 9, a user conducts a procedure on the patient 112 using the robotic system 100 and the tool assembly 230 by following normal operating procedures. While the user conducts the surgical procedure, the robotic system 100 measures torque and rotation of one or more motors, such as motor M1, using one or more sensors, such as the torque sensor T1 and the rotary encoder R1. The system 100 determines in real time values of force and position of the cable C1 engaged with the motor M1 based on the measured torque and rotation of the motor M1, and the system 100 then calculates the derivatives of force and position of the cable C1 from the values of force and position. The system 100 then detects when a current value of the derivative of force or position exceeds a predetermined threshold value, and take a variety of actions based on the exact configuration of the system 100 (as outlined above). For example, the system 100 can alert the user of an imminent cable failure. The system 100 can then enter a safe mode or pause operation, or the system 100 can continue to operate under normal parameters and allow the user to decide how to proceed. The user can then remove the tool assembly 230 prior to a complete cable failure or terminate a current function of the end effector 238.

Figure 10:
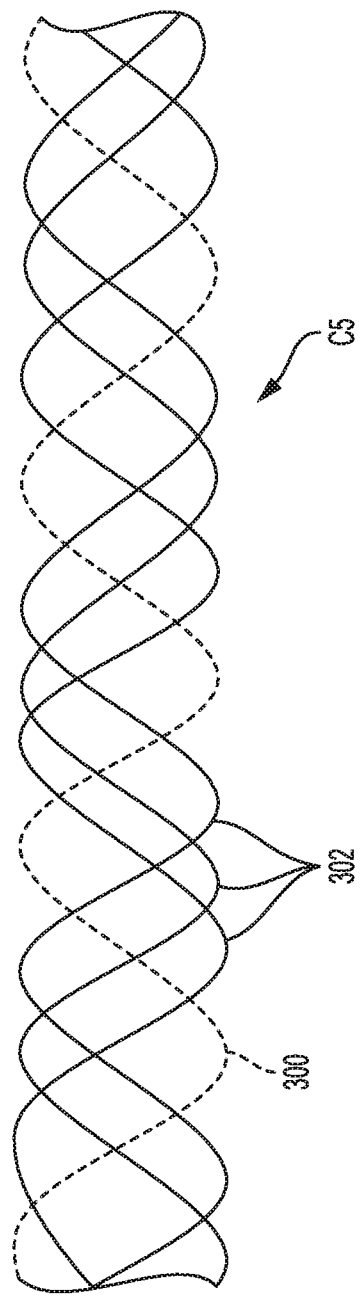
FIG. 10 illustrates another embodiment of a cable with a sacrificial filament therein.

The filaments provided in the cable C1 are all identical to each other. In other embodiments, however, a cable C5 can incorporate one or more sacrificial filaments 300 therein at known locations, as illustrated in FIG. 10. These sacrificial filaments 300 are designed to be weaker than one or more normal filaments 302 in the cable C5 by having lower tensile strength and are thus configured to fail at an earlier point than other filaments 302 in the cable C5. For example, in some embodiments the sacrificial filaments 300 can be about 1% to 50% weaker than the regular filaments 302, and/or can be designed to fail at around 0 to (n/2) life cycles earlier than the regular filaments 302. When the one or more sacrificial filaments 300 fail, the system can detect the failure of the sacrificial filament 300 and determine that the normal filaments 302 may likewise fail soon. The system can thus alert a user (e.g., in the manner described above) to the imminent failure of the entire cable C5 while being able to determine exactly where the current failed filaments are located because the location of the sacrificial filaments 300 are known, considering the cable C5 was designed to fail at that point.

In some embodiments sacrificial filament 300 has the same appearance of filaments 302, but in other embodiments, the sacrificial filament can have a variety of different configurations and/or forms. For example, the filament can be electrically conductive or nonconductive. The filament can have a different shape than other filaments, such as being flat, a different color, or it can have some other visually distinctive difference to help distinguish it from surrounding filaments. While the sacrificial filament 300 is used with the robotic system discussed herein such that the system can detect the failure of the filament, similar sacrificial filaments can be incorporated into other devices that do not rely on a robotic system. For example, the sacrificial filament can be incorporated into any cable driven device and designed to fail to indicate that the remaining filaments in the cable have the potential for imminent failure. The failure can be detected in numerous ways, such as through electromagnetic, electrical, optical, and ultrasonic means. As noted above, monitoring of one or more cables can be conducted for virtually any cable that controls any function of the end effector. One example of a function for which the potential for cable failure is particularly useful is articulation of the end effector.

Operation of Control System

Generally, as discussed above, the control system can control movement and actuation of a surgical device. For example, the control system can include at least one computer system and can be operably coupled to the at least one motor that drives a drive system on the surgical device. The computer system can include components, such as a processor, that are configured for running one or more logic functions, such as with respect to a program stored in a memory coupled to the processor. For example, the processor can be coupled to one or more wireless or wired user input devices ("UIDs"), and it can be configured for receiving sensed information, aggregating it, and computing outputs based at least in part on the sensed information. These outputs can be transmitted to the drive system of surgical device to control the surgical device during use.

In certain embodiments, the control system can be a closed-loop feedback system. The stored data within the computer system can include predetermined threshold(s) for one or more stages of operation of the drive system. When the control system is actuated, it drives one or more motors on or coupled to the surgical device, consequently actuating the drive system through each stage of operation. During each stage of operation, the control system can receive feedback input from one or more sensors coupled to the motor(s) that sense displacement and/or torque of the motor(s). The computer system can aggregate the received feedback input(s), perform any necessary calculations, compare it to the predetermined threshold for the corresponding stage of operation, and provide output data to the motor(s). If at any time during each stage of operation the control system determines that the received input exceeds a maximum predetermined threshold or is less than a minimum predetermined threshold, the control system can modify the output data sent to the motor based on the programmed logic functions. For example, the control system can modify the output data sent to the motor(s) to reduce a current delivered to the motor to reduce motor force or a voltage delivered to the motor to thereby reduce a rotational speed of the motor(s) or to stop movement of the motor(s).

Referring back to FIGS. 1-3, the control system 115, which includes at least one computer system, can be operably coupled (wired or wirelessly) to each of the motors M1-M7 that drive the various components of the drive systems. In particular, the control system 115 can monitor a force applied to and a position of each of the motors M1-M7 and can thus monitor a force on and position of one or more of the cables C1-C4, can compare the monitored values to various threshold forces, and can modify or terminate current operating procedures as a result.

As discussed above, the control system disclosed herein can be implemented using one or more computer systems, which may also be referred to herein as digital data processing systems and programmable systems.

One or more aspects or features of the control systems described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, e.g., a mouse, a trackball, etc., by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Figure 11:
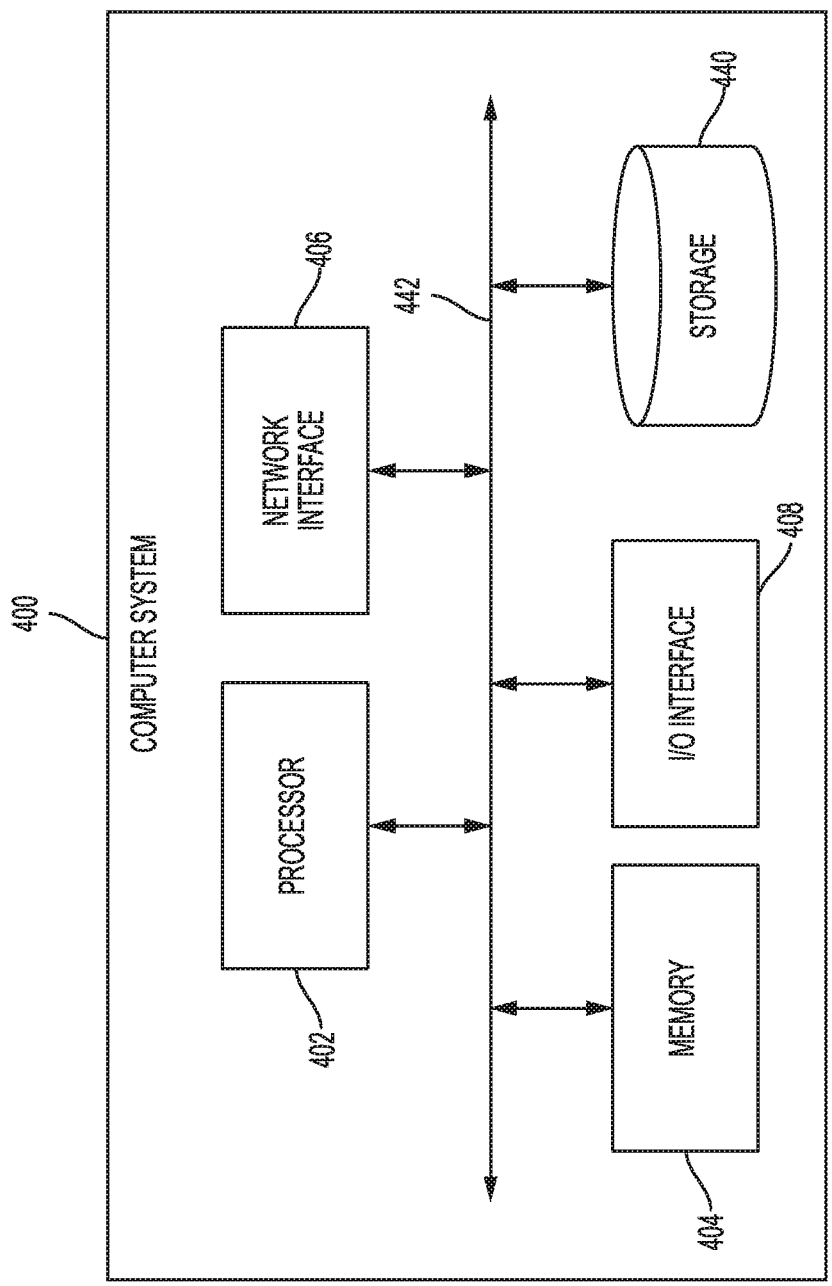
FIG. 11 illustrates one exemplary embodiment of a computer system that can be used to implement a control system of the present disclosure.

FIG. 11 illustrates one exemplary embodiment of a computer system 400. As shown, the computer system 400 includes one or more processors 402 which can control the operation of the computer system 400. "Processors" are also referred to herein as "controllers." The processor(s) 402 can include any type of microprocessor or central processing unit (CPU), including programmable general-purpose or special-purpose microprocessors and/or any one of a variety of proprietary or commercially available single or multi-processor systems. The computer system 400 can also include one or more memories 404, which can provide temporary storage for code to be executed by the processor(s) 402 or for data acquired from one or more users, storage devices, and/or databases. The memory 404 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 400 can be coupled to a bus system 412. The illustrated bus system 412 is an abstraction that represents any one or more separate physical busses, communication lines/interfaces, and/or multi-drop or point-to-point connections, connected by appropriate bridges, adapters, and/or controllers. The computer system 400 can also include one or more network interface(s) 406, one or more input/output (IO) interface(s) 408 that can include one or more interface components, and one or more storage device(s) 410.

The network interface(s) 406 can enable the computer system 400 to communicate with remote devices, e.g., motor(s) coupled to the various drive systems that are located within the surgical device or a robotic surgical system or other computer systems, over a network, and can be, for non-limiting example, remote desktop connection interfaces, Ethernet adapters, and/or other local area network (LAN) adapters. The IO interface(s) 408 can include one or more interface components to connect the computer system 400 with other electronic equipment, such as the sensors located on the motor(s). For non-limiting example, the IO interface(s) 408 can include high speed data ports, such as universal serial bus (USB) ports, 1394 ports, Wi-Fi, Bluetooth, etc. Additionally, the computer system 400 can be accessible to a human user, and thus the IO interface(s) 408 can include displays, speakers, keyboards, pointing devices, and/or various other video, audio, or alphanumeric interfaces. The storage device(s) 410 can include any conventional medium for storing data in a non-volatile and/or non-transient manner. The storage device(s) 410 can thus hold data and/or instructions in a persistent state, i.e., the value(s) are retained despite interruption of power to the computer system 400. The storage device(s) 410 can include one or more hard disk drives, flash drives, USB drives, optical drives, various media cards, diskettes, compact discs, and/or any combination thereof and can be directly connected to the computer system 400 or remotely connected thereto, such as over a network. In an exemplary embodiment, the storage device(s) 410 can include a tangible or non-transitory computer readable medium configured to store data, e.g., a hard disk drive, a flash drive, a USB drive, an optical drive, a media card, a diskette, a compact disc, etc.

The elements illustrated in FIG. 11 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 400 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 400 can also include a web server for generating and/or delivering the web pages to client computer systems.

In an exemplary embodiment, the computer system 400 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A robotic surgical system, comprising:
   an end effector assembly having a shaft with an end effector disposed at a proximal end thereof, the end effector having at least one function, the end effector having a torque sensor;
   a drive system operably coupled to the end effector assembly and operably coupled to at least one motor, the drive system having at least one cable, the drive system configured to drive the at least one function on the end effector through actuation of the at least one cable; and
   a control system configured to actuate the at least one motor to drive the drive system and thereby control actuation of the at least one function of the end effector, the control system configured to preemptively detect potential imminent failure of the at least one cable of the drive system;
   wherein the torque sensor is operably coupled with the at least one motor, the control system is configured to record force applied to the cable by the motor, calculate a derivative of force applied to the cable, alert a user if the derivative of force applied to the cable exceeds a predetermined threshold value, and set a second lower threshold value if the predetermined threshold value is exceeded.

2. The robotic surgical system of claim 1, wherein the threshold value is determined by recording a running average of the derivative of force.

3. The robotic surgical system of claim 1, wherein the end effector assembly includes a rotary encoder.

4. The robotic surgical system of claim 3, wherein the control system is configured to record a position of the cable, calculate a derivative of position of the cable, and alert a user if the derivative of position exceeds a threshold value.

5. The robotic surgical system of claim 1, wherein the at least one cable includes a sacrificial filament therein, the sacrificial filament being configured to fail at a lower force relative to remaining filaments in the at least one cable.

6. A surgical tool, comprising:
   a housing;
   an end effector assembly having a shaft with an end effector disposed at a proximal end thereof, the end effector having at least one function, the end effector assembly operationally engageable with the housing;
   a drive system operably coupled to the end effector assembly and operably coupled to at least one motor, the drive system having at least one cable, the drive system configured to drive the at least one function on the end effector through actuation of the at least one cable; and
   a control system disposed in the housing and in communication with the motor and one or more sensors in the surgical tool, the control system being configured to actuate the at least one motor to drive the drive system, the control system configured to monitor a status of the at least one cable based on data from the sensors;
   wherein the surgical tool has a first, normal mode of operation and a second, alert mode of operation, and the control system is configured to transition the surgical tool from the first mode to the second mode upon detecting an imminent failure of the at least one cable when monitoring the status of the cable based on the data from the sensors, and the second mode causes jaws on the end effector assembly to close and one or more wrist joints on the end effector assembly to align with a longitudinal axis of the end effector.

7. The surgical tool of claim 6, wherein the sensors include at least one of a torque sensor and a rotary encoder.

8. The surgical tool of claim 7, wherein the control system is configured to record at least one of a force on or a position of the cable, calculate a derivative value of the recorded value, and alert a user if the derivative value exceeds a predetermined threshold value.

9. The surgical tool of claim 8, wherein the predetermined threshold value is a multiple of a running average of the derivative value.

10. The surgical tool of claim 6, wherein the at least one cable includes a sacrificial filament therein, the sacrificial filament being configured to fail at a lower force relative to remaining filaments in the at least one cable.

11. The surgical tool of claim 6, wherein the end effector includes one of a stapler, a cutter, a grasper, or a suturing head.

12. The surgical tool of claim 6, wherein the at least one function of the end effector is articulation of the end effector.

13. A method comprising:
 inserting a surgical tool within a patient, the surgical tool having jaws and one or more wrist joints;
 operating a surgical tool under normal operating conditions, during which a control system of the surgical tool monitors an integrity indicator of one or more cables therein and alerts a user of an imminent cable failure of the one or more cables, wherein the surgical tool enters a safe mode of operation when the control system detects a potential for an imminent cable failure of the one or more cables in which the jaws on the surgical tool close and the one or more wrist joints on the surgical tool to align with a longitudinal axis of the surgical tool; and
 removing the surgical tool from the patient upon being alerted by the control system of an imminent cable failure of the one or more cables.

14. The method of claim 13, wherein the control system monitors at least one of torque and rotation of one or more motors in the surgical tool using one or more sensors.

15. The method of claim 14, wherein the control system calculates derivatives of at least one of force and position of the one or more cables based on values from the torque and rotation of the one or more motors, and detects when a current value of one or both of the derivatives of force and position exceeds a threshold value.

* * * * *